United States Patent
Yao et al.

(10) Patent No.: US 9,562,063 B2
(45) Date of Patent: Feb. 7, 2017

(54) PROCESS FOR THE PREPARATION OF DOPO-DERIVED COMPOUNDS AND COMPOSITIONS THEREOF

(71) Applicant: Albemarle Corporation, Baton Rouge, LA (US)

(72) Inventors: Qiang Yao, Baton Rouge, LA (US); Junuzo Wang, Little Rock, AR (US); Arthur G. Mack, Prairieville, LA (US)

(73) Assignee: Albemarle Corporation, Baton Rouge, LA (US)

(*) Notice: Subject to any disclaimer, the term of this patent is extended or adjusted under 35 U.S.C. 154(b) by 0 days.

(21) Appl. No.: 15/220,261

(22) Filed: Jul. 26, 2016

(65) Prior Publication Data

US 2016/0333039 A1    Nov. 17, 2016

Related U.S. Application Data

(60) Continuation of application No. 14/594,703, filed on Jan. 12, 2015, now abandoned, which is a division of application No. 13/638,482, filed as application No. PCT/US2011/030183 on Mar. 28, 2011, now Pat. No. 9,012,546.

(60) Provisional application No. 61/319,580, filed on Mar. 31, 2010, provisional application No. 61/410,694, filed on Nov. 5, 2010.

(51) Int. Cl.
| | | |
|---|---|---|
| *C07F 9/6571* | (2006.01) | |
| *B01J 27/138* | (2006.01) | |
| *B01J 31/02* | (2006.01) | |
| *C08K 5/53* | (2006.01) | |

(52) U.S. Cl.
CPC ........ *C07F 9/657163* (2013.01); *B01J 27/138* (2013.01); *B01J 31/0225* (2013.01); *C07B 2200/07* (2013.01)

(58) Field of Classification Search
None
See application file for complete search history.

(56) References Cited

U.S. PATENT DOCUMENTS

| 6,440,067 B1 | 8/2002 | DeLuca et al. |
| 7,053,138 B2 | 5/2006 | Magendie et al. |
| 7,671,147 B2 | 3/2010 | Urakawa et al. |
| 2003/0034482 A1 | 2/2003 | Kinoshita et al. |
| 2005/0038278 A1 | 2/2005 | Dittrich et al. |
| 2005/0038279 A1 | 2/2005 | Dittrich et al. |
| 2006/0102882 A1 | 5/2006 | Bedner et al. |
| 2006/0247344 A1 | 11/2006 | Mueller et al. |
| 2007/0060673 A1 | 3/2007 | Tobisawa et al. |
| 2012/0053265 A1* | 3/2012 | Angell .............. C07F 9/657172 523/451 |
| 2012/0055705 A1* | 3/2012 | White ............... C07F 9/657172 174/259 |

FOREIGN PATENT DOCUMENTS

| DE | 102007028593 | 12/2008 |
| JP | 11106619 A | 4/1999 |
| JP | 2001270993 A | 10/2001 |
| JP | 2001-053633 A | 2/2002 |
| JP | 2002-193985 A | 7/2002 |
| WO | 2008/119693 A1 | 10/2008 |
| WO | 2010/135393 A1 | 11/2010 |
| WO | 2010/135398 A1 | 11/2010 |

OTHER PUBLICATIONS

Johannes Artner, et al; "A Novel DOPO-Based Diamine as Hardener and Flame Retardant for Epoxy Resin Systems"; Macromolecular Materials and Engineering; 2008; vol. 293; pp. 503-514; 2008 Wiley-VCH Verlag GmbH & Co. KGaA, Weinheim, Germany.

Schartel, B. et al.; "Pyrolysis and Fire Behaviour of Epoxy Systems Containing a Novel 9, 10-dihydro-9-oxa-10- phosphaphenanthrene-10-oxide-(DOPO)-based Diamino Hardener"; European Polymer Journal; 2008; vol. 44; pp. 704-715; 2008 Elsevier Ltd.

Johannes Artner, et al.; "A Novel and Effective Synthetic Approach to 9, 10-Dihydro-9-oxa-10-phosphapenanthrene-10-oxide-(DOPO) Derivatives"; Phosphorus, Sulfur, and Silicon; 2007; vol. 182; pp. 2131-2148; Taylor & Francis Group, LLC.

Edward D. Weil; "Flame Retardants, Phosphorus"; Kirk-Othmer Encyclopedia of Chemical Terminology; pp. 484-540; vol. 11; Online—Posted Dec. 4, 2000; John Wiley & Sons, Inc.; US.

Abrunhosa-Thomas, I.; Sellers, Claire E.; and Montchamp, J.; "Alkylation of H-Phosphinate Esters under Basic Conditions"; Journal of Organic Chemistry; 2007; vol. 72, pp. 2851-2856.

* cited by examiner

*Primary Examiner* — Michael J Feely
(74) *Attorney, Agent, or Firm* — James A. Jubinsky; Marcy M. Hoefling; Nathaniel C. Dunn

(57) ABSTRACT

This invention relates to a process for producing compounds derived from 9,10-Dihydro-9-Oxa-10-Phosphaphenantrene-10-oxide (DOPO). In particular, the invention relates to producing DOPO-derived compounds by reacting DOPO with diol compounds in the presence of a catalyst. This invention also relates to DOPO derived composition containing a high melting point diastereomer. The DOPO derived compounds may be useful as flame-retardants.

11 Claims, No Drawings

PROCESS FOR THE PREPARATION OF DOPO-DERIVED COMPOUNDS AND COMPOSITIONS THEREOF

This application is a continuation of U.S. application Ser. No. 14/594,703(now abandoned), filed Jan. 12, 2015, which is a divisional of U.S. application Ser. No. 13/638,482 (now U.S. Pat. No. 9,012,546), filed on Sep. 28, 2012, which is a national stage entry (371) of International Patent Application No. PCT/US2011/030183, filed Mar. 28, 2011, which claims the benefit and priority of U.S. Application No. 61/319,580, filed Mar. 31, 2010 and 61/410,694, filed on Nov. 5, 2010.

TECHNICAL FIELD

This invention relates to a process for producing compounds derived from 9,10-Dihydro-9-Oxa-10-Phosphaphenantrene-10-oxide (DOPO). In particular, the invention relates to producing DOPO-derived compounds by reacting DOPO with diol compounds in the presence of a catalyst. This invention also relates to DOPO derived composition containing a high melting point diastereomer. The DOPO derived compounds may be useful as flame-retardants.

BACKGROUND

Phosphorus-containing flame-retardants are perceived to be more environmentally friendly than halogen containing flame-retardants. In the field of epoxy resins and laminates, organo-phosphorous flame-retardants with reactive groups, such as those derived from 9,10-Dihydro-9-Oxa-10-Phosphaphenantrene-10-oxide (DOPO), are commonly used in epoxy resin formulations because they react with the epoxy to form a phosphorus-modified epoxy resin. However, "additive" organophosphorus flame-retardants, which do not have reactive groups, are typically not used in epoxy formulations, since it is believed that covalent bonding between the epoxy resin and a reactive organophosphorus flame retardant are needed to provide high glass transition temperatures and dimensional stability.

DOPO-derived additive compounds, useful as flame-retardants, have been produced by reacting DOPO with halogen-containing compounds (see Japanese Kokai Patent Application No. Hei 11[1999]-106619 and Japanese Kokai Patent Application No. P2001-270993A). However, DOPO-derived compounds have not heretofore been produced by reacting DOPO with diol compounds in the presence of a catalyst.

SUMMARY OF THE INVENTION

The present invention relates a process for preparing the compound of Formula I:

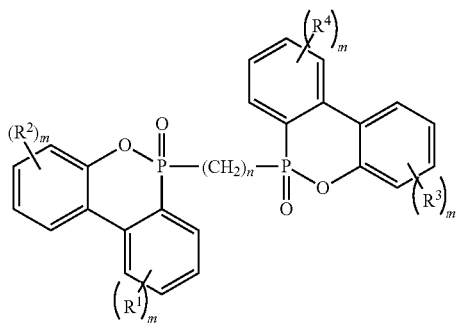

Formula I where each $R^1$, $R^2$, $R^3$ and $R^4$ are independently hydrogen, $C_1$-$C_{15}$ alkyl, $C_6$-$C_{12}$ aryl, $C_7$-$C_{15}$ aralkyl or $C_7$-$C_{15}$ alkaryl; or $R^1$ and $R^2$ or $R^3$ and $R^4$ taken together can form a saturated or unsaturated cyclic ring, wherein said saturated or unsaturated cyclic ring may be optional substituted by a $C_1$-$C_6$ alkyl; each m is independently 1, 2, 3 or 4; and n is 2 to about 18; comprising reacting a compound of Formula A:

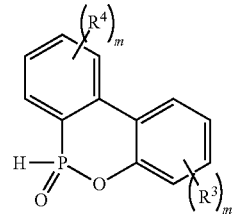

Formula A where $R^3$, $R^4$ and m are defined above;
with a diol compound of Formula B in the presence of a catalyst, optionally a solvent, and optionally an entrainer;

$$HO-(CH_2)_n-OH$$

Formula B wherein n is defined above.

This invention also relates to a composition comprising the diastereomer of Formula IIa:

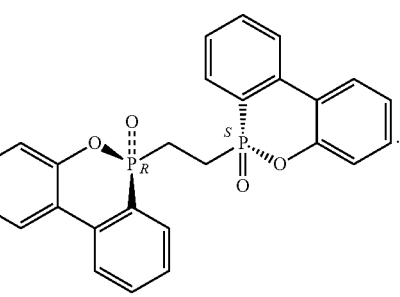

Formula IIa

DETAILED DESCRIPTION OF THE INVENTION

The present invention relates a process for preparing the compound of Formula I:

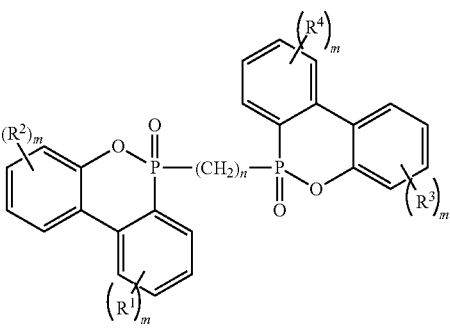

Formula I where each $R^1$, $R^2$, $R^3$ and $R^4$ are independently hydrogen, $C_1$-$C_{15}$ alkyl, $C_6$-$C_{12}$ aryl, $C_7$-$C_{15}$ aralkyl or $C_7$-$C_{15}$ alkaryl; or $R^1$ and $R^2$ or $R^3$ and $R^4$ taken together can form a saturated or unsaturated cyclic ring, wherein said saturated or unsaturated cyclic ring may be optional substituted by a $C_1$-$C_6$ alkyl; each m is independently 1, 2, 3 or 4; and n is 2 to about 18; comprising reacting a DOPO compound of Formula A:

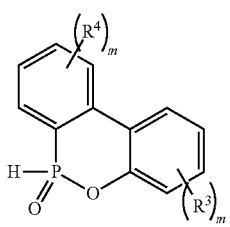

Formula A where $R^3$, $R^4$ and m are defined above;
with a diol compound of Formula B in the presence of a catalyst, optionally a solvent, and optionally an entrainer;

HO—(CH$_2$)$_n$—OH    Formula B wherein n is defined above.

The reaction is essentially a dehydration reaction of DOPO tautomer phosphonites with diols, followed by an Arbuzov rearrangement producing the DOPO dimer derived compound (DiDOPO compound) and water.

One embodiment of the present invention is where n is 2 to 6 and $R^1$, $R^2$, $R^3$ and $R^4$ are all hydrogen.

Another embodiment of the present invention is a process for preparing the compound of Formula II:

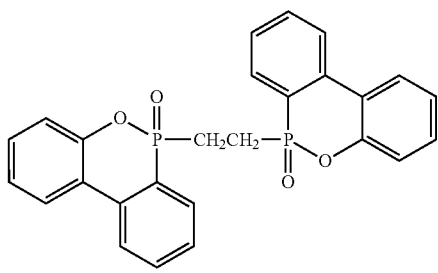

Formula II (6H-Dibenz[c,e][1,2]oxaphosphorin, 6,6'-(1,2-ethanediyl)bis-, 6,6'-dioxide)

comprising reacting a DOPO compound of Formula C:

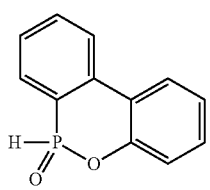

Formula C with ethylene glycol in the presence of a catalyst, optionally a solvent and optionally an entrainer.

One embodiment in the process for making the compounds of Formulas I or II is where the entrainer is present. Another embodiment in the process for making the compounds of Formulas I or II is where the solvent is present. Another embodiment in the process for making the compounds of Formulas I or II is where both the solvent and the entrainer are present.

The molar ratios of diol compound of Formula B or ethylene glycol to DOPO compounds of Formula A or IIA respectively may range from about 0.5 to 100, or about 0.5 to 10, or about 0.6 to 5. If the ratio is too low, it leads to insufficient conversion of DOPO. If the ratio is too high, it results in a large recycling of ethylene glycol.

In one embodiment, the diol compound or ethylene glycol with the catalyst described below is slowly introduced into the DOPO, or DOPO/optional solvent/optional entrainer mixture.

The catalyst that may be used is any suitable catalyst for the dehydration and Arbuzov reactions. General suitable catalysts are alky halides, alkali halides, alkaline earth metal halides, transition metals and their halides or acid catalysts. Arbuzov reaction catalysts are especially suitable.

Examples of catalysts that may be used include, but are not limited to: sodium iodide, lithium bromide, lithium chloride, potassium iodide, potassium bromide, lithium iodide, $C_1$-$C_6$ alkyl iodide, C1-$C_6$ alkyl bromide, 2-iodoethanol, 2-bromoethanol, 2-chloroethanol, 3-iodopropanol, 3-bromopropanol, ferric bromide, ferrous chloride, ferrous bromide, manganous halide, copper powder, nickel halide, cobalt chloride, cesium bromide, palladium chloride, sulfuric acid, aryl sulfonic acid, alkyl sulfonic acid, arylalkyl sulfonic acid, hydrochloric acid, hydrobromic acid, hydrofluoric acid, oxalic acid, perchloric acid, trifluoromethane sulfonic acid, fluorosulfonic acid, nitric acid, aluminum chloride, diethyl aluminum chloride, triethylaluminum/hydrogen chloride, ferric chloride, zinc chloride, antimony trichloride, stannic chloride, boron trifluoride, acidic zeolites, acidic clays, polymeric sulfonic acids, or mixtures thereof.

The catalyst may be added in concentrations ranging from about 0.01 wt % to about 10 wt %, or about 0.1 to about 5%, or about 0.1 wt % to about 2.5 wt %, based on the total weight of the DOPO compound.

The temperature of the reaction may range from about 100° C. to about 250° C., or about 150° C. to 220° C. or about 170° C. to about 210° C.

The reaction may use an optional solvent. The solvent should be chosen so that it will ideally dissolve all or substantially all of the DOPO reactant.

Since the temperature of the reaction will typically be above 100° C., it is preferable that a high boiling point solvent be used. A high boiling point solvent, is a solvent having a boiling point greater than about 150° C. at 1 atmosphere and a melting point greater than about −100° C. Examples of high boiling point solvents, include, but are not limited to: diphenylmethane, diphenylethane, diphenylpropane, biphenyl, decahydronaphthalene, cyclohexylbenzene, 1,3-diisopropylbenzene, dimethyl sulfoxide (DMSO), dimethyl formamide (DMF), dimethylacetamide (DMAC), ethylene glycol dimethyl ether, ethylene glycol diethyl ether or mixtures thereof.

Lower boiling point solvents may also be used, but in order to get the temperature high enough, the reaction would be conducted under pressure such that the reaction pressure will be equal to or higher than the vapor pressure of the solvent at the reaction temperature. Depending on the solvent, the reaction pressure for lower boiling point solvents would range from greater than 1 atmosphere to about 10 atmosphere, or greater than 1 atmosphere to about 5 atmosphere, or greater than 1 atmosphere to about 3 atmosphere.

Low boiling point solvents are solvents having a boiling point less than about 150° C., or about 100° C. at 1 atmosphere. Examples of low boiling point solvents, include, but are not limited to heptane, hexane, petroleum ether, methylcyclohexane; toluene, xylene, mesitylene, ethyl benzene, tetrahydrofuran, 1,4-dioxane, acetonitrile or mixtures thereof.

The amount of solvent in the reaction may range from 0 wt % to about 95 wt %, or about 30 wt % to about 85 wt %, or about 60 wt % to about 80 wt %, based on the total weight of the reactant mixture (e.g., reactants, catalysts, solvents and entrainer if present).

Since the reaction generates water, it is advantageously to use an entrainer to remove water in order to push the reaction forward. An entrainer is an organic solvent that can form azeotropes with water. The entrainer is usually chemically inert organic liquid whose boiling points are below reaction temperature, for example, 150° C., and form azeotropes with water.

In one embodiment, the entrainer is a low boiling point solvent, wherein the low boiling point solvent has a boiling point lower than about 150° C. at 1 atmosphere.

Examples of entrainers that may be used, include, but are not limited to pentane, hexane, heptane, octane, cyclohexane, methylcyclohexane, toluene, xylenes, ethylbenzene, isopropylbenzene or mixtures thereof.

The amount of entrainer required for complete removal of the water can be determined in manner from the water formation calculated according to the stoichiometry of the reaction and from the composition of the binary or ternary azeotrope. It has been found useful to use the entrainer in excess, advantageously in an amount, which is from 50 to 200% by weight above the theoretically calculated amount.

The entrainer may or may not be same as the solvent. If the entrainer is different from the solvent, the amount of entrainer may range from about 0 wt % to about 30 wt %, or about 1 wt % to about 30 wt %, or about 2 wt % to about 15 wt %, based on the total weight of the reactant mixture (e.g., reactants, catalysts, solvents and entrainer if present).

In a particularly useful embodiment of the process of the invention, the entrainer is added to the reaction mixture before the diol or ethylene glycol compounds. After a gentle reflux is observed, addition of diol or ethylene glycol with catalyst is started. The progress of the reaction can be followed in a simple manner by collection and separation of the entrainer/water/diol mixture distilled off. The entrainer and diol separated from the azeotrope can be returned directly, i.e. without an intermediate purification step, to the reaction.

In one embodiment, the process is conducted at the normal pressure and the entrainer is continuously recycled back to reactor.

The entrainer can also be replaced by vacuum and/or inert gases such as nitrogen, carbon dioxide, and/or helium as long as the water generated in the process can be removed effectively.

The reaction may be carried out in batch or continuous mode. A series of reaction vessels with mixers may be used for continuous mode. When in continuous mode, an excess of diol compound or ethylene glycol is used and can be recycled back into the process for further reaction.

The reaction time may vary depending on the reaction temperature, type and amount of catalyst, and the use, type and amount of a solvent and/or entrainer. Typically, the reaction time will be from about 0.5 to about 48 hours or about 1 to about 24 hours.

After the reaction, the resulting product of Formulas I or II may be purified using any conventional method such as washing distillation, filtration and/or drying. In one embodiment, water or water miscible solvents such as alcohols (e.g., isopropanol), aldehydes or ketones (e.g., acetone) are used to wash the product before and/or after filtration.

The peak melting point of the compound of Formula II is preferably greater than about 245° C. or about 250° C. For determining peak melting point, a differential scanning calorimeter (DSC) may be used such as a "TA Instruments Q200" analyzer with its standard DSC cell. The DSC is connected to a PC, which provides user interface and operational system control. The temperature scale is calibrated at 10° C./min using the melting points of gallium, indium, lead and zinc reference standards. The heat flow scale is calibrated using the heat of fusion of indium. The baseline response is calibrated at 20° C./min with a synthetic sapphire heat capacity standard. All of these calibrations should be performed according to the instrument manufacturers recommended procedures.

The samples are run in gold plated stainless steel crucible at 10° C./min from 0° C. to 400° C. A raw data file containing the sample heat flow and temperature data is saved to the PC hard drive during the measurement. After the DSC measurement is finished the raw data file is analyzed for melt behavior. The melting endotherm is integrated to yield, extrapolated onset temperature, peak temperature and heat of fusion.

The TA Instrument software is used to determine the peak melting point by selecting temperature points above and below the peak. If a sample exhibits multiple peaks, then multiple peak melting points will be reported. The peak melting point is the maximum endotherm for a particular melting transition. The peak maximum determination is an analysis used to determine the most remote point, relative to the baseline, within the chosen limits.

High Melting Point Diastereomer Composition

This invention also relates to a composition comprising the diastereomer of Formula IIa:

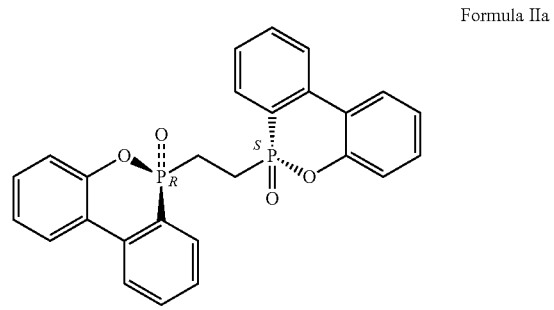

Formula IIa

It has been discovered that by using the process of the present invention, a mixtures of stereoisomers are produced. For the compound of Formula II, at least three stereoisomers are produced in the composition. One is the high melting point diastereomer of Formula IIa and two are lower melting point enantiomers of Formula IIb and IIc.

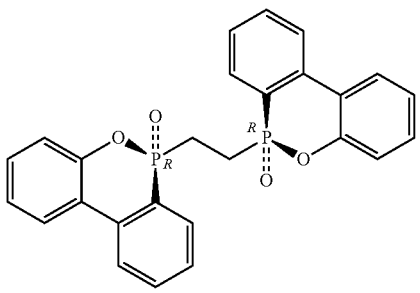

Formula IIb

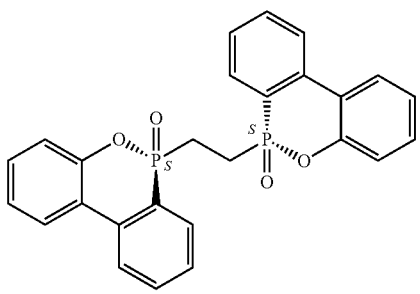

Formula IIc

It is sometimes beneficial to choose a composition with higher amount of high melting point constituents. A composition with a higher "Isomer Ratio" of high melting point constituents vs. low melting point constituents would be more desirable for high temperature polymer applications.

In the preset application, the Isomer Ratio may be calculated from DSC curves as follows:

Isomer Ratio=$A_h/(A_h+A_l)$, wherein $A_h$: area of high melting point peak and $A_l$: area of low melting point peak.
Another method of calculating the Isomer Ratio is from $^{31}$P NMR as follows:

Corrected ratio=$(A_h-A_l\times 0.5)/(A_h+A_l)$, wherein $A_h$: area of high field peak and $A_l$: area of low field peak.

The uncorrected ratio=$A_h/(A_h+A_l)$, wherein $A_h$ and $A_l$ are defined above.

It has been found that a corrected ratio obtained from $^{31}$P NMR is close to values obtained from DSC curves and therefore a corrected ratio is always assumed if there is no explicit statement about the Isomer Ratios obtained from $^{31}$P NMR.

31P NMR Method:

One NMR spectroscopy procedure that may be used to measure the Isomer Ratio is discussed below. This procedure is suitable for the determination of Isomer Ratio by weight percent normalization.

Nucleus: 31P; Proton decoupled; Pulse program: zgig30; Collected data points (TD): 205 k; Spectral Width (SWH): ~40322 Hz; Pre-pulse delay (D1): 20 sec minimum (use adequate prepulse delay to ensure all observed nuclei have adequate relaxation time); Acquisitions (NS): 16 scans minimum (enough scans to provide good signal to noise); Lock Solvent: CDCl3. Referenced to 85% aqueous phosphoric acid.

The chemical shift of the high melting point isomer appears at the high magnetic field region around 36.9 ppm and the chemical shift of the low melting point isomers appears at the low field region around 37.1 ppm.

It is one embodiment, the composition comprises a plurality of the diastereomer of Formula IIa. In other embodiments, the composition has an Isomer Ratio of greater than about 0.5, or greater than about 0.6, or greater than about 0.7, or greater than about 0.8, or greater than about 0.9, or greater than about 0.95 or greater than about 0.98, based on using DSC or 31P NMR Method. For the 31P NMR Method, the Isomer Ratio is the corrected Isomer Ratio.

Process to Achieve Higher Melting Point Isomers:

In another embodiment, the present invention relates to a method for producing a higher melting point composition comprising the compound of Formula II:

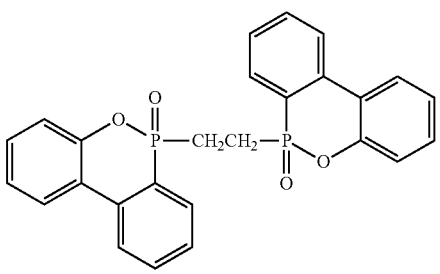

Formula II comprising contacting a composition containing lower amounts of high melting point isomers of Formula II, with alcohols, water, or mixtures thereof in the presence of an acid catalyst, thereby producing a composition containing larger amounts of higher melting point isomers of Formula II.

Low melting point isomers can be converted to high melting point isomers in the presence of alcohols and/or water at a temperature ranging from 0 to 300° C. This isomerization is catalyzed by acid catalysts that include mineral acids and Lewis acids. Mineral acids include sulfuric acid, methanesulfonic acid, hydrochloric acid, phosphoric acid, phosphonic acids and phosphinic acids. Lewis acids are defined as a molecular entity that is an electron pair acceptor and include aluminum chloride, zinc chloride, ferric chloride, etc.

Examples of such acid catalysts include, but are not limited to: sulfuric acid, aryl sulfonic acid, alkyl sulfonic acid, aralkyl sulfonic acid, hydrochloric acid, hydrobromic acid, hydrofluoric acid, oxalic acid, perchloric acid, trifluoromethane sulfonic acid, fluorosulfonic acid, nitric acid, phosphoric acid, phosphonic acids, phosphinic acids aluminum chloride, diethyl aluminum chloride, triethylaluminum/hydrogen chloride, ferric chloride, zinc chloride, antimony trichloride, stannic chloride, boron trifluoride, acidic zeolites, acidic clays, polymeric sulfonic acids, or mixtures thereof One embodiment to carry out the isomerization is to feed a mixture of alkylene glycol (e.g., ethylene glycol) and water to the DOPO solution at a temperature of 25 to 300° C. under elevated pressure or normal pressure. Because the reaction of DOPO+alkylene glycol produces water in-situ, the mixture of alkylene glycol and water can be replaced by pure alkylene glycol provided that the generated water is not completely removed in a timely manner so that it can participate the isomerization. Otherwise, a mixture of alkylene glycol and water is required. This mixture can be the recovered alkylene glycol and water, which are co-distilled out and condensed during the reaction, or they can be obtained by mixing alkylene glycol with water.

The mixture of alkylene glycol and water can be added at the beginning of the reaction where the conversion of DOPO is essentially zero, during the reaction, and/or after the reaction where DOPO is essentially consumed up. If the mixture of alkylene glycol and water is added after DOPO is consumed up, the mixture can be replaced by water alone, alcohols or their combinations since they do not interfere with the reaction any more except isomerization.

A preferred embodiment of the above process is when the alkylene glycol is ethylene glycol.

The required acid catalysts are preferably those generated in-situ during the reaction; however, external acids can be added to accelerate both the reaction and isomerization.

A second embodiment includes the treatment of finished compounds of Formula I or II containing small amount (e.g., <15%) of high melting point isomers by alcohols and/or water in the presence of acid catalysts and in the presence or absence of solvents under elevated pressure or normal pressure at a temperature range of 25 to 300° C. The treatment is performed by mixing alcohols, and/or water, acid catalysts, and DiDOPO containing small amount (e.g., <15% by weight) of high melting point isomer(s). This mixture is then heated to a temperature range of 25-300° C. for a length of time until the desired isomer ratio is obtained. Usually the length of time varies from a few minutes to 10 hours, preferably from 0.5 to 8 hours, more preferably from 1 to 5 hours. The amount of catalyst is from 0.1% to 50% of DiDOPO, preferably from 1 to 25%, more preferably from 5 to 15%. The temperature is from 25 to 300° C., preferably from 50 to 250° C., more preferably from 80 to 200° C. This method is particularly advantageous to convert the finished DiDOPO that is largely composed of low melting point isomers to high melting point DiDOPO.

Use of the Compounds of the Invention

This invention also related to a flame retardant polymer composition comprising a polymer and the flame retardant amount of the compounds of Formula I, II, IIa, IIb, IIc or mixtures thereof.

Polymer that may be used in the flame retardant polymer composition include, but are not limited to: polyolefins, polyesters, polyethers, polyketones, polyamides, polyvinylchlorides, natural and synthetic rubbers, polyurethanes, polystyrenes, poly(meth)acrylates, phenolic resins, polybenzoxazine, polyacetals, polyacrylonitriles, polybutadienes, polystyrenes, polyimides, polyamideimides, polyetherimides, polyphenylsulfides, polyphenylene oxide, polycarbonates, cellulose, cellulose derivatives, cyanate esters, polyphenylene esters, polybutadiene resins, butadiene-styrene resins, butadiene-divinylbenzene-styrene resins, epoxy-modified polybutadiene resins, acrylic or vinyl acetate adhesives, carboxyl-terminated butadiene-acrylonitrile copolymers, phenylene ethers, maleic anhydride-grafted butadiene-styrene copolymers, maleic anhydride-modified 4-methyl-1pentene resins, maleated 1-butene-ethylene copolymers, resins derived from vinylbenzyl ether compounds, epoxy resins or mixtures thereof. Preferably, the polymers are polyolefins, polyesters, phenolic resins, phenol triazine novolaks, cresol triazine novolaks, triazine phenol epoxy novolaks, triazine cresol epoxy novolaks, polyamides, polyurethanes, polystyrene, epoxy resins or mixtures thereof.

Another embodiment is when the flame retardant composition further comprises at least one conventional additive, such as heat stabilizers, light stabilizers, ultra-violet light absorbers, anti-oxidants, anti-static agents, preservatives, adhesion promoters, fillers, pigments, dyes, lubricants, mold releasers, blowing agents, fungicides, plasticizers, processing aids, acid scavengers, dyes, pigments, nucleating agents, wetting agents, dispersing agents, synergists, mineral fillers, reinforcing agents such as glass fiber, glass flake, carbon fiber, or metal fiber; whiskers such as potassium titanate, aluminum borate, or calcium silicate; inorganic fillers and other fire-retardant additives, smoke suppressants and mixtures thereof.

The other flame retardant additives which may be used with the compounds of Formulas Formula I, II, IIa, IIb, IIc or mixtures thereof include, but are not limited to, nitrogen-containing synergists such as ammonium polyphosphate, melamine, melamine phosphate, melamine cyanurate, melamine pyrophosphate, melamine polyphosphate, phosphate and cyanurate derivatives of guanidine and piperazine, phosphazene compound, polyphophazenes, antimony oxide, silica, talc, hydrotalcite, borate salts, hydrated alumina such as aluminum hydroxide (ATH), boehmite, bismuth oxide, molybdenum oxide, or mixtures of these compounds with zinc, aluminum and/or magnesium oxide or salts.

The amount of compounds of Formula I, II, IIa, IIb, IIc or mixtures thereof added to the polymer as a flame retardant may be varied over a wide range. Usually from about 0.1 to about 100 parts by weight of the compounds are used per 100 parts by weight of polymer. Preferably about 0.5 to about 70 parts of the compounds are used per 100 parts by weight of polymer, or from about 2 to about 50 parts by weight per 100 parts by weight of polymer.

Preferably, the compounds of Formula I, II, IIa, IIb, IIc or mixtures thereof are grounded or milled prior to combining with the polymer. The $d_{50}$ particle size after grinding or milling may be less than about 15 μm, or less than 10 μm, or less than about 5 μm, or less than about 3 μm or less than about 2 μm. The $d_{50}$ particle size may even be less than 1 μm, such as about 100 nm to 800 nm. A particle size of $d_{50}$ is the median particle size, where half the particles are above the value and half the particles are below the value. Any suitable milling or grinding technique may be used such as jet milling.

To determine median particle size, a Coulter LS-230 counter or equivalent is used with its small volume module. The operating instructions of the manufacturer are followed. Alternatively, a Horiba laser light scattering instrument (e.g., Horiba LA900 Model 7991) or equivalent can be used. The procedure involves weighing the sample, typically an amount in the range of about 0.01 gram to about 0.015 gram, into a clean dry aluminum cup that has been washed with deionized water before use. The instrument autosampler disperses a 0.05 g sample in water using 0.4 ml of 1% Triton X-100 surfactant and ultrasonic treatment. This suspension is circulated through a measuring cell where the powder particles scatter a beam of laser light. Detectors in the instrument measure intensity of the light scattered. The computer in the instrument calculates mean particle size, average particle size and particle size distribution from such measurements.

Masterbatches of polymer containing the compounds of Formula I, II, IIa, IIb, IIc or mixtures thereof of this invention, which is blended with additional amounts of substrate polymer, can contain even higher concentrations of the compounds e.g., from about 10 to about 1000, or from about 25 to about 500, or from about 25 to about 250 parts by weight of the compounds per 100 parts by weight of polymer.

Alternatively, the amount of the phosphorus compounds of Formula I, II, IIa, IIb, IIc or mixtures thereof in the flame retardant polymer composition is selected so the composition will contain about 0.1 wt % to about 10 wt %, or about 1.0 wt % to about 7 wt %, or about 1.2 wt % to about 5 wt %, or about 1.5 wt % to about 4 wt % phosphorous content, based on the total weight of the composition.

EXAMPLES

The following Examples illustrate the present invention. It is to be understood, however, that the invention, as fully described herein and as recited in the Claims, is not intended to be limited by the details of the following Examples.

Example 1

6H-Dibenz[c,e][1,2]oxaphosphorin, 6,6'-(1,2-ethanediyl)bis-, 6,6'-dioxide

To a 25 ml 3-necked reaction flask fitted with a Dean-Stark trap, addition funnel, thermocouple, and nitrogen inlet and outlet were charged 17.082 g DOPO (0.0790 mole), 2.509 g ethylene glycol (0.0404 mole) and 0.300 g sodium iodide (0.00200 mole). The reaction mixture was heated to 210° C. and the addition of p-xylene (entrainer) from addition funnel was started. The water immediately came out with p-xylene and ethylene glycol. After the reaction temperature was maintained between 190-210° C. for 2 hours, another 1.651 gram of ethylene glycol was added to compensate those lost. The reaction mixture was kept stirring for one more hour and then the mixture was diluted with xylene and stirred for half hour at 133° C. The slurry was filtered, washed by acetone and dried at 120° C. overnight. A white solid of 14.84 grams was obtained and the yield was 82%.

Example 2

6H-Dibenz[c,e][1,2]oxaphosphorin, 6,6'-(1,2-ethanediyl)bis-, 6,6'-dioxide

To a 250 ml 3-necked reaction flask fitted with a Dean-Stark trap, two addition funnels, thermocouple, and nitrogen inlet and outlet was charged 80.64 g (0.373 mole) DOPO. The flask was heated and the temperature was brought to 170° C. The addition of p-xylene from one addition funnel was started. After a gentle reflux of xylene in Dean-Stark trap was observed, a mixture of 16.682 g (0.269 mole) ethylene glycol with 1.019 g methylsulfonic acid was gradually added from the $2^{nd}$ addition funnel. The reaction mixture was kept stirring at a temperature range of 170-180° C. for 18 hours, then the reaction temperature was lowered to 100° C. The obtained slurry was washed by a mixture of 140 g water and 11.06 g 50% sodium hydroxide, then filtered, washed by water and dried in an oven. A white solid of 42.125 g corresponding a yield of 50% was obtained. The uncorrected 31PNMR isomer ratio of high melting point isomer/low melting point isomer=0.87. The corrected ratio was 0.80.

This example demonstrates that by keeping reaction temperature low so that water removal was not timely a product with very high content of high melting point isomer was obtained.

Example 3

6H-Dibenz[c,e][1,2]oxaphosphorin, 6,6'-(1,2-ethanediyl)bis-, 6,6'-dioxide

To a 500 ml 4-necked reaction flask equipped with a Dean-Stark trap, a mechanical stirrer, two addition funnels, thermocouple, and nitrogen inlet and outlet were charged 87.30 g (0.404 mole) DOPO, 27.4 g p-xylene, and 178 g diphenylpropane. The mixture was brought to a temperature of 200° C. and more p-xylene was added to ensure a gentle reflux in Dean-Stark trap. Addition of a mixture of 43.037 g (0.693 mole) ethylene glycol and 0.884 g sodium iodide was then started and completed in 5.5 hours. A mixture of aqueous distillate was recycled back to the addition funnel and the addition was completed in 6 hours. A slurry was observed with good stirrability. A sample was taken and 31P NMR indicated the slurry was composed of 93% DiDOPO and 7% other phosphorus-containing species. The slurry was mixed with 19 g isopropanol and stirred for half hour at a temperature of 86° C., then it was filtered, washed by 2×40 g isopropanol, and dried in an oven at a temperature of 130° C. overnight. A white solid of 81.2 g was obtained with a purity >99%. The isolated yield was 88%. The uncorrected isomer ratio of high melting point isomer/low melting point isomer=0.69. The corrected ratio was 0.53.

This example demonstrates that by feeding a mixture of ethylene glycol and water during the reaction a product rich in the high melting point isomer(s) was obtained.

Example 4

6H-Dibenz[c,e][1,2]oxaphosphorin, 6,6'-(1,2-ethanediyl)bis-, 6,6'-dioxide

To a 250 ml 3-necked reaction flask equipped with a Dean-Stark trap, a magnetic, two addition funnels, thermocouple, and nitrogen inlet and outlet were charged 46.778 g (0.216 mole) DOPO, 16.50 g p-xylene, and 106.70 g diphenylmethane. The mixture was brought to a temperature of 200° C. and more p-xylene was added to ensure a gentle reflux in Dean-Stark trap. Addition of a mixture of 25.407 g (0.393 mole) ethylene glycol and 0.639 g sodium iodide was then started and completed in 6 hours. A mixture of aqueous distillate was recycled back to the addition funnel and the addition was completed in 2 hours. A slurry was observed with very good stirrability. A sample was taken and $^{31}$P NMR indicated the slurry was composed of 93% DiDOPO and 7% other phosphorus-containing species.

Example 5

6H-Dibenz[c,e][1,2]oxaphosphorin, 6,6'-(1,2-ethanediyl)bis-, 6,6'-dioxide

Following example 4, but biphenyl was used as a solvent. The slurry of the final mixture was composed of 91% DiDOPO and 9% other phosphorus-containing species.

Example 6

6H-Dibenz[c,e][1,2]oxaphosphorin, 6,6'-(1,3-propanediyl)bis-, 6,6'-dioxide

To a 100 ml 3-necked reaction flask equipped with a Dean-Stark trap, a magnetic, two addition funnels, thermocouple, and nitrogen inlet and outlet were charged 33.004 g (0.153 mole) DOPO and 5.361 g p-xylene. The mixture was brought to a temperature of 200° C. then the addition of a mixture of 7.405 g (0.0973 mole) 1,3-propanediol and 0.631 g sodium iodide was started and completed 1.6 hours. A mixture of aqueous distillate was recycled back to the addition funnel and the addition was completed in 1 hour. Repeat this procedure two times and a sample was taken. $^{31}$P NMR indicated the solution was composed of 55% DiDOPO, 30% mono-species and 15% other phosphorus-containing species.

Example 7

High Pressure Process
6H-Dibenz[c,e][1,2]oxaphosphorin,
6,6'-(1,2-ethanediyl)bis-, 6,6'-dioxide To a 100 mL autoclave equipped with a mechanic stirrer, thermocouple, distillation head, and collection vessel were charged 10.80 g DOPO, 3.1 g ethylene glycol, 50 g p-xylene (solvent/entrainer) and 0.188 g sodium iodide. The reaction mixture was first swept by nitrogen flow for 15 minutes and then gradually brought to a temperature range of 190-200° C. under 40-41 psig. Liquid started to come out at 194° C. After no more liquid out, the reaction temperature was slowly raised to 200° C. and the mixture was easily stirred for 2 hours. After cooling down and degassing, NMR analysis showed the crude slurry contained 62% DiDOPO, 22% DOPO and the rest of being phosphorus-containing species. Another 0.78 g of ethylene glycol and 28 g of p-xylene were added into reactor and heated to 190-200° C. After 5 hours, the reaction mixture was cooled down and diluted with 22 g of p-xylene and 10 g of iso-propanol. NMR analysis indicated 90% DiDOPO.

Example 8

6H-Dibenz[c,e][1,2]oxaphosphorin,
6,6'-(1,2-ethanediyl)bis-, 6,6'-dioxide with a
relatively low Isomer Ratio To a 500 ml 4-necked reaction flask equipped with a Dean-Stark trap, a mechanical stirrer, two addition funnels, thermocouple, and nitrogen inlet and outlet were charged 88.36 g (0.409 mole) DOPO, 43.60 g p-xylene, and 177 g diphenylmethane. The mixture was brought to a temperature of 200° C. to obtain a gentle reflux in Dean-Stark trap. Addition of a mixture of 61.84 g (0.996 mole) ethylene glycol and 0.925 g sodium iodide was then started and completed in 14.5 hours. A sample was taken and $^{31}P$ NMR indicated the slurry was composed of 82% DiDOPO, 9% phosphonic acid and other phosphorous-containing species. The uncorrected ratio of high melting point isomer(s)/total isomers=0.41. The corrected ratio is 0.12. This example demonstrates that by feeding ethylene glycol free of water a product rich in the low melting point isomers was obtained. A summary of some of the Examples is shown below in Table 1.

TABLE 1

SUMMARY OF EXAMPLES

| | Example | | | | | | |
|---|---|---|---|---|---|---|---|
| | 1 | 2 | 3 | 4 | 5 | 7 | 8 |
| Charge mode | DOPO/EG catalyst Charged once | EG/cat. added continuously | EG/cat. added continuously and recycled | EG/cat. added continuously and recycled | EG/cat. added continuously and recycled | DOPO/EG/catalyst Charged once, closed system | EG/cat. added continuously without recycle |
| Catalyst | NaI | Methylsulfonic acid | NaI | NaI | NaI | NaI | NaI |
| Temp (° C.) | 190-210 | 170-175 | 190-200 | 190-200 | 190-200 | 190-200 | 190-200 |
| Entrainer | p-xylene | p-xylene | p-xylene | p-xylene | p-xylene | xylene | xylene |
| Solvent | No | No | Diphenypropane | Diphenylmethane | Biphenyl | xylene | Diphenylmethane |
| CrudeYield | | | 93% | 91% | 92% | 90% | 82% |
| Isolated yield | 82% | 50% | 88% | 83% | | | |
| Stirrability | Difficult | Kind of difficult | Easy | Very Easy | Very Easy | Good | Easy |
| Ratio by $^{31}P$ NMR | 0.51 | 0.87 | 0.69 | 0.62 | 0.58 | 0.57 | 0.41 |
| Ratio by $^{31}P$ NMR-corrected | 0.26 | 0.80 | 0.53 | 0.43 | 0.37 | 0.36 | 0.12 |
| Ratio by DSC | | 0.82 | 0.61 | | | | |

Corrected ratio = (area of low field peak − 0.5* area of high field peak)/(area of low field peak + area of high field peak)

Example 9

6H-Dibenz[c,e][1,2]oxaphosphorin, 6,6'-(1,2-ethanediyl)bis-, 6,6'-dioxide

To a 500 ml 3-necked reaction flask fitted with a Dean-Stark trap, an addition funnel, thermocouple, and nitrogen inlet and outlet was charged 89.0 g (0.412 mole) DOPO, 40.9 g p-xylene, 182.8 g diphenylmethane. The mixture was heated and the temperature was brought to 200° C. After a gentle reflux of xylene in Dean-Stark trap was observed, a mixture of 61.895 g ethylene glycol with 0.918 g sodium iodide was gradually added from the addition funnel. The reaction mixture was kept stirring at a temperature range of 190-200° C. After about 16 hours, the mixture of EG/NaI was used up and a recovered 48 mL EG/H2O from distillate was fed continuously at a temperature range of 200-25° C. and completed in 4 hours. Then the mixture was then heated back to 190° C. to remove ethylene glycol and water in ~1 hour. After cooled down, the reaction mixture was subjected to filtration and isopropanol washes, and then dried at 130° C. Samples were taken during the reaction and the isomer ratios were measured by $^{31}$P NMR. Since the reaction generated by-products, the isomer ratios were normalized. The results are shown in Table 2.

TABLE 2

HIGH MELTING POINT (MP) ISOMER CONTENT VS. TIME OF REACTION IN EXAMPLE 9

| Time (hrs) | EG/NaI remaining (ml) | EG/H₂O added (ml) | Phosphonic acid (mole %) | DOPO conversion (%) | High Mp Isomer (% uncorrected) | High MP Isomer (%, corrected) |
|---|---|---|---|---|---|---|
| 13.5 | 6 |  | 9 | 93 | 44 | 17 |
| 14.6 | 2 |  | 11 | 98 | 49 | 24 |
| 16.1 | 0 | 0 | 11 | 100 | 52 | 28 |
| 17.1 |  | 5 | 11 |  | 52 | 28 |
| 18.1 |  | 12 | 11 |  | 61 | 41 |
| 20.6 |  | 25 | 11 |  | 60 | 40 |
| 21.6 |  | 48 | 11 |  | 88 | 82 |

This example demonstrates that high melting point isomer(s) can be obtained by converting low melting point isomer by ethylene glycol and water in the presence of acid catalysts.

Example 10

6H-Dibenz[c,e][1,2]oxaphosphorin, 6,6'-(1,2-ethanediyl)bis-, 6,6'-dioxide

A 6H-Dibenz[c,e][1,2]oxaphosphorin, 6,6'-(1,2-ethanediyl)bis-, 6,6'-dioxide composition (7.866 g) containing 88% low melting point isomer was mixed with 85% aqueous phosphoric acid (0.189 g) and diphenylpropane (42 g). The mixture was gradually heated to 200° C. and was kept at this temperature for 2.5 hours. Samples were taken during the treatment and measured by 31P NMR. The results were shown in Table 3 below:

TABLE 3

ISOMER CONTENT VS. REACTION TIME FOR EXAMPLE 10

| Time (hrs) | Low Mp Isomers % | High mp Isomer % |
|---|---|---|
| 0 | 88 | 12 |
| 1 | 81 | 19 |
| 2.5 | 48 | 52 |

This example demonstrates that treating 6H-Dibenz[c,e][1,2]oxaphosphorin, 6,6'-(1,2-ethanediyl)bis-, 6,6'-dioxide rich in low melting point isomers by aqueous acid catalyst at high temperature increased content of high melting point isomer.

Example 11

6H-Dibenz[c,e][1,2]oxaphosphorin, 6,6'-(1,3-propanediyl)bis-, 6,6'-dioxide

6H-Dibenz[c,e][1,2]oxaphosphorin, 6,6'-(1,2-ethanediyl)bis-, 6,6'-dioxide composition (57.9 g isomer ratio=0.43, low melt isomer=0.57) was mixed with 134.5 g diphenylmethane, and 3.1 g 85% phosphoric acid in a flask equipped with additional funnel, Dean-Stark trap, mechanic stirrer, and thermocouple. The mixture was heated to 150° C. Water (13 g) was slowly added to the reaction mixture and continuously distilled out. After 12 ml water was collected, the reaction was set to the total reflux and the reaction mixture was stirred for 2.5 hours at this temperature. Then the reaction temperature was lowered to 126° C. and isopropanol (70.4 g) isopropanol was added. The mixture was subsequently cooled, filtered, washed by 82 g isopropanol and dried at 130° C. in an oven overnight. A sample was taken and $^{31}$P NMR result showed an isomer ratio of 0.90 (low melt isomer=0.10).

This example demonstrates that treating 6H-Dibenz[c,e][1,2]oxaphosphorin, 6,6'-(1,2-ethanediyl)bis-, 6,6'-dioxide rich in low melting point isomers by water in the presence of an acid catalyst increased the content of high melting point isomer.

Example 12

6H-Dibenz[c,e][1,2]oxaphosphorin, 6,6'-(1,3-propanediyl)bis-, 6,6'-dioxide

To a 1 L reaction flask equipped with mechanic stirrer, thermometer, pressure gauge, and Dean-Stark trap were charged with 100.00 g DOPO, 0.10 g sodium iodide, 0.28 g ethylene glycol, and 400 g mixed xylenes. The reaction mixture was heated to 200° C. under about 40 psig. A solution of 0.90 g sodium iodide in 50.00 g ethylene glycol was gradually fed to the mixture in a course of 14 hours. Subsequently the mixture was kept to stir at 198-200° C. for 6 hours. A slurry sample was then taken. $^{31}$P NMR showed that DOPO was essentially consumed with a product isomer ratio=0.43 and the presence of phosphonic acid (about 3 mole % of DOPO). In order to increase the isomer ratio, water (120 g) was slowly fed to the reaction mixture at 173° C. in a course of 5 hours. At the end of the water treatment, a sample was taken and $^{31}$P NMR showed a product isomer ratio=0.94.

This example demonstrates that high melting point isomer(s) can be obtained by converting low melting point isomer by water.

Example 13

Use of 6H-Dibenz[c,e][1,2]oxaphosphorin, 6,6'(1,2-butanediyl)bis-, 6,6'-dioxide as a flame retardant in epoxy laminate

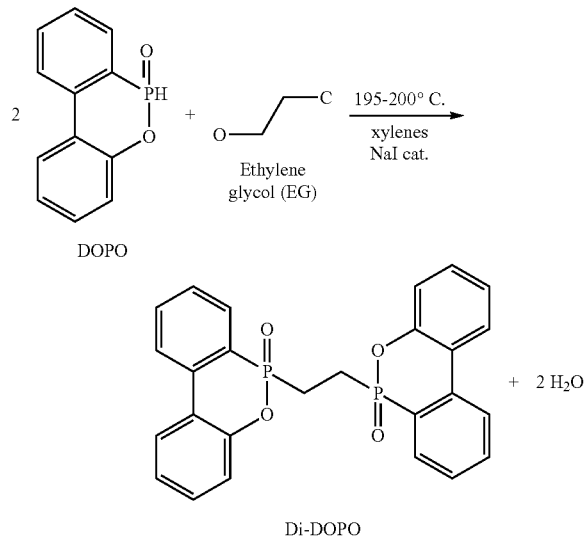

High purity DOPO was loaded into a reactor and a given amount of mixed xylenes was then pumped into the reactor. A 2.62 wt % NaI/EG solution was prepared and charged to the reactor. The contents were then agitated and heated to 198° C. in 5-6 hours while the pressure was maintained at 40-41 psig. Once the contents reached the reaction temperature, a co-feed containing the 2.62 wt % NaI/EG and mixed xylenes was started. The co-feed lasted a minimum of about 14 hours.

The xylene feed rate was on the order of 1 lb/min. After an 11.5-hour feed and 2-hour hold, the reactor became full. It was cooled to 190° C., and a sample of the reactor slurry was collected. NMR results indicated that the DOPO conversion was about 72% at this point. The reactor was re-heated to 197-199° C., and the co-feed was conducted for another 5 hours, followed with 2.5 hour hold. The DOPO conversion was then about 93% at the end of the second co-feed. The reaction mixture was quenched with IPA and cooled slowly to −100° C.

Once cooled, the contents of the reactor were filtered and the wetcake was then washed three times with fresh IPA and vacuum dried at 130° C.

Approximately 100 g of the sample prepared above was added to a 2 L Erlenmeyer flask, along with 2.0 kg of chloroform and 0.4 kg of 2-propanol. The mixture was stirred for about 15 minutes at 65° C. The mixture was removed from heat and allowed to cool slowly without stirring to room temperature. The erlenmeyer was then placed in an ice bath for about 1 hour. The white solid was vacuum filtered through a medium glass fritted funnel, rinsed with about 100 mL of 2-propanol and dried at 170° C. for 5 h. Three batches of the resultant dried powder were combined and jet-milled to smaller particle size having a d50 of about 2 to 4 μm to afford 130 g of a very high purity 6H-Dibenz[c,e][1,2]oxaphosphorin, butanediyl)bis-, 6,6'-dioxide flame retardant sample. The isomer ratio of the sample was about 0.98.

In general, stock solutions of advanced resin, curative and promoter are all prepared and stored separately to facilitate experimentation. A 50 wt % o-cresolphenol epoxy novolac resin solution, NPCN®-703 (Nan Ya Plastics Corporation), containing 50 wt % 2-butanone (MEK) was prepared. Durite SD-1702 novolac curing agent was obtained from Hexion Corporation. A novolac resin solution was prepared by dissolving 50 wt % SD-1702 in 50 wt % MEK solvent.

A flame retardant resin mixture containing 3.0 wt % P was prepared by blending 128.8 g of 50 wt % NPCN 703 solution, 62.7 g of 50 wt % SD-1702 solution, 14.0 g of the flame retardant, 14.0 g of melamine polyphosphate Melapur 200 (M-200) from BASF Corporation and 0.070 g 2-phenylimidazole promoter. An additional 11 g MEK was added to the mixture. The novolac to promoter ratio was about 448. The flame retardant was insoluble in the resin solution until making contact with the hot gel plate, where it dissolved completely at high temperature. About 0.5-1 mL of the resin mixture was added to a hot cure plate (Thermo-electric company) at about 170-172° C. A tongue depressor was split in half lengthwise, and half of the depressor was used to move the resin on the hot plate until stiffness was noted and then lifting the resin with the flat part of the depressor until string formation ceased. The gel time was 3 minutes, 16 seconds, determined by the point where resin "strings" could no longer be pulled from the resin mixture and the epoxy became "tack free". The resin mixture was mixed thoroughly using a high shear mixer stirred at 6,000 rpm for about 15 minutes.

An 11 inch by 11 inch square woven glass fabric (7628 glass with 643 finish from BGF Industries) was cut to size from a large roll and stapled to wood supports (12 inches long, 1 inch wide and 1/16 inch thick) on the top and bottom ends of the fabric. The wood supports contained holes in the corners for inserting paper clips on one end for hanging the fabric in the B-stage oven. The A-stage, or resin varnish, was painted on the front and back of the fabric. Paper clips were unfolded and inserted into the both holes of one wood support. The resin-saturated fabric was hung from aluminum supports in a laboratory fume hood and allowed to drip dry for about one minute before hanging in a pre-heated (to 170° C.) forced air Blue M oven (Lab Safety Supply Inc., a unit of General Signal) for 1 minute, 20 seconds. The edges of the B-staged prepreg were removed by reducing the sheet dimensions to 10 inch by 10 inch. The sheet was cut into four 5 inch by 5 inch sheets and weighed before stacking the four layers of prepreg between two layers of Pacothane release film (Insulectro Corp.) and two steel plates (1/8 inch thick, 12 inch by 12 inch square dimensions). The laminate was formed in the hot press at 5,000 psig for 1 hour. The resulting laminate was 0.03 inches thick, contained 45.5 wt % resin and underwent 17 wt % resin overflow during pressing. Five 0.5 inch wide coupons were cut from the laminate using a diamond saw, and the coupon edges were smoothed with sandpaper. The flammability of the coupons were screened by ASTM D3801-06 using an Atlas UL-94 burn chamber, resulting in a V-0 rating with 29 seconds total burn time for the two ignitions on all five coupons. No single burn was greater than 10 seconds.

The glass transition temperature of the laminate was about 185° C. and the TGA was about 322° C. for a 1% loss, about 342° C. for a 2% loss and about 363° C. for a 5% loss.

Components referred to by chemical name or formula anywhere in the specification or Claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the Claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

The invention described and claimed herein is not to be limited in scope by the specific examples and embodiments herein disclosed, since these examples and embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended Claims.

The invention claimed is:

1. A process for preparing a compound of Formula I:

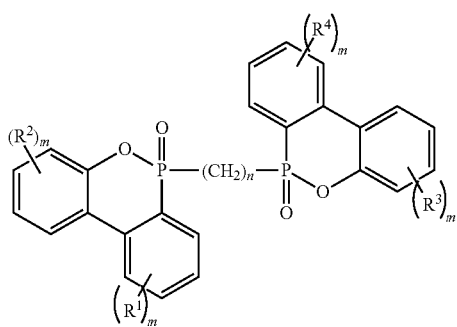

Formula I wherein each $R^1$, $R^2$, $R^3$ and $R^4$ are independently hydrogen, $C_1$-$C_{15}$ alkyl, $C_6$-$C_{12}$ aryl, $C_7$-$C_{15}$ aralkyl or $C_7$-$C_{15}$ alkaryl; or $R^1$ and $R^2$ or $R^3$ and $R^4$ taken together form a saturated or unsaturated cyclic ring, wherein said saturated or unsaturated cyclic ring is optionally substituted by a $C_1$-$C_6$ alkyl; each m is independently 1, 2, 3 or 4; and n is 2 to about 18;

comprising reacting a compound of Formula A with a diol compound of Formula B in the presence of a catalyst, optionally a solvent, and optionally an entrainer:

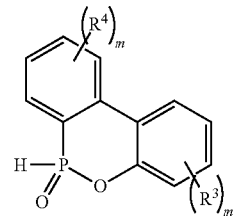

Formula A wherein $R^3$, $R^4$ and m are defined above;

Formula B wherein n is defined above.

2. The process of claim 1, wherein n is 2 to 6 and $R^1$, $R^2$, $R^3$ and $R^4$ are hydrogen.

3. The process of claim 1, wherein both the solvent and the entrainer are present.

4. The process of claim 1, wherein said catalyst is an alkyl halide, an alkali halide, an alkaline earth metal halide, a transition metal, a transition metal halide, or an acid catalyst.

5. The process of claim 1, wherein the reaction takes place at a temperature ranging from about 100° C. to about 250° C.

6. The process of claim 1, wherein the reaction takes place in a reactor, the reaction produces water, and wherein the water and the diol compound of Formula B are continuously recycled back to the reactor.

7. The process of claim 1, wherein the catalyst is an acid catalyst.

8. The process of claim 7, wherein said acid catalyst is sulfuric acid, aryl sulfonic acid, alkyl sulfonic acid, aralkyl sulfonic acid, hydrochloric acid, hydrobromic acid, hydrofluoric acid, oxalic acid, perchloric acid, trifluoromethane sulfonic acid, fluorosulfonic acid, nitric acid, aluminum chloride, diethyl aluminum chloride, triethylaluminum/hydrogen chloride, ferric chloride, zinc chloride, antimony trichloride, stannic chloride, boron trifluoride, acidic zeolites, acidic clays, polymeric sulfonic acids, or mixtures thereof.

9. A process for preparing a compound of Formula II:

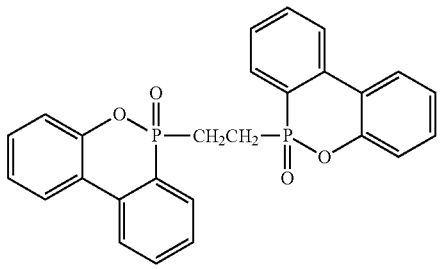

Formula II comprising reacting a compound of Formula C with ethylene glycol in the presence of a catalyst, optionally a solvent, and optionally an entrainer:

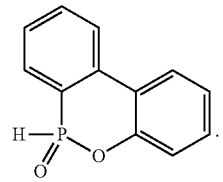

Formula C

10. A method of increasing a content of high melting point isomers in a mixture of stereoisomers comprising contacting a composition containing initial amounts of high melting point diastereomers of Formula IIa, and initial amounts of low melting point enantiomers of Formulas IIb and IIc:

Formula IIa

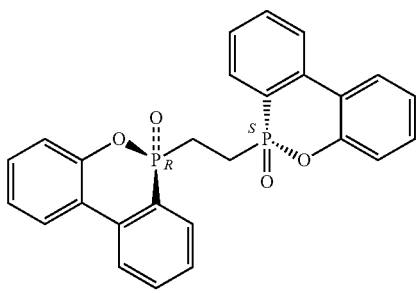

Formula IIb

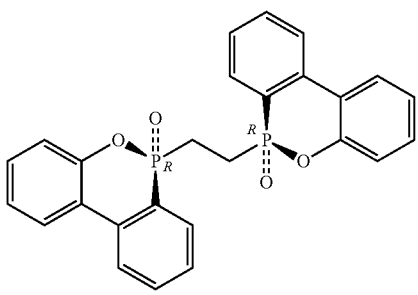

Formula IIc

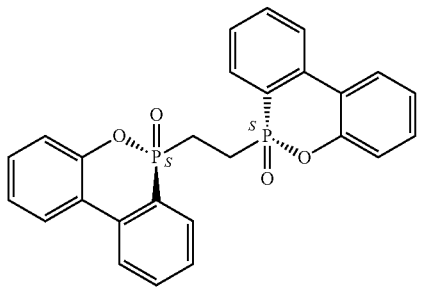

with alcohols, water, or mixtures thereof, in the presence of an acid catalyst to convert at least a portion of the low melting point enantiomers of Formulas IIb and IIc to high melting point diastereomers of Formula IIa.

11. The method of claim 10, wherein said acid catalyst is sulfuric acid, aryl sulfonic acid, alkyl sulfonic acid, aralkyl sulfonic acid, hydrochloric acid, hydrobromic acid, hydrofluoric acid, oxalic acid, perchloric acid, trifluoromethane sulfonic acid, fluorosulfonic acid, nitric acid, phosphoric acid, phosphonic acids, phosphinic acids, aluminum chloride, diethyl aluminum chloride, triethylaluminum/hydrogen chloride, ferric chloride, zinc chloride, antimony trichloride, stannic chloride, boron trifluoride, acidic zeolites, acidic clays, polymeric sulfonic acids, or mixtures thereof.

* * * * *